United States Patent [19]
Harris et al.

[11] Patent Number: 4,691,029
[45] Date of Patent: Sep. 1, 1987

[54] PROCESS FOR PRODUCING 3-THIENYLMALONIC ACID

[75] Inventors: Patrick C. Harris, Leatherhead; John A. Wilcox, Capel, both of England

[73] Assignee: Beecham Group p.L.c., England

[21] Appl. No.: 641,330

[22] Filed: Aug. 16, 1984

Related U.S. Application Data

[63] Continuation of Ser. No. 434,245, Oct. 14, 1982, abandoned, which is a continuation of Ser. No. 297,704, Aug. 31, 1981, abandoned, which is a continuation of Ser. No. 156,188, Jun. 3, 1980, abandoned.

[30] Foreign Application Priority Data

Jun. 19, 1979 [GB] United Kingdom ............... 7921385

[51] Int. Cl.$^4$ .................................... C07D 333/24
[52] U.S. Cl. ................................................ 549/79
[58] Field of Search ...................................... 549/79

[56] References Cited

U.S. PATENT DOCUMENTS 2,513,140 6/1950 Campaigne et al.

FOREIGN PATENT DOCUMENTS 1139164 1/1969 United Kingdom.

OTHER PUBLICATIONS

Rabinovitch and Winkler, Kinetics of the Alkaline Hydrolysis of Propionitrile, Can. Jnl. of Research, vol. 20, Sec. B, pp. 185–188.
Wagner et al, "Synthetic Organic Chemistry", (1965) pp. 412–415.
Morrison et al, "Organic Chemistry", 2nd ed. (1966), pp. 470–471.
Rappoport, "The Chem. of the Cyano Group", (1970), pp. 256–259.

Primary Examiner—Alan Siegel
Attorney, Agent, or Firm—Jacobs & Jacobs

[57] ABSTRACT

A process for preparing 3-thienyl malonic acid, comprising treatment of a 3-thienyl cyanoacetate of formula (III):

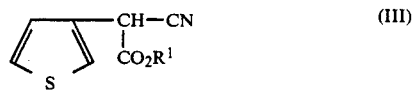

where $R^1$ represents an aryl or alkyl group, with at least a molar excess of an alkali metal hydroxide.

5 Claims, No Drawings

PROCESS FOR PRODUCING 3-THIENYLMALONIC ACID

This application is a continuation of application Ser. No. 434,245 filed Oct. 14, 1982, which is a continuation of Ser. No. 297,704 filed Aug. 31, 1981, which is a continuation of Ser. No. 156,188 filed June 3, 1980, all now abandoned.

This invention relates to a chemical process for the production of 3-thienylmalonic acid, a compound useful as an intermediate in the production of penicillins of general formula (I):

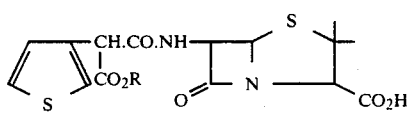
(I)

The compound of formula (I) in which R is hydrogen is disclosed in our British Pat. No. 1,004,670, and the sodium salt thereof is known as ticarcillin. Compounds of formula (I) in which R is an alkyl, aralkyl or ring substituted aralkyl group are disclosed in our British Pat. No. 1,125,557 and compounds of formula (I) in which R is aryl are disclosed in our British Pat. No. 1,133,886.

In British Pat. No. 1,125,557 the penicillin of formula (I) was prepared from a 3-thienylacetonitrile via 3-thienylacetic acid and a diester of 3-thienylmalonic acid. It has now been found that 3-thienylmalonic acid can be prepared in good yield in a one-step process directly from a 3-thienyl cyanoacetate.

Accordingly the present invention provides a process for the preparation of 3-thienylmalonic acid of formula (II):

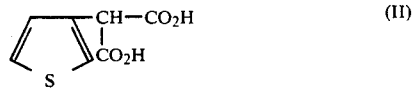
(II)

which process comprises the treatment of a 3-thienyl cyanoacetate of formula (III):

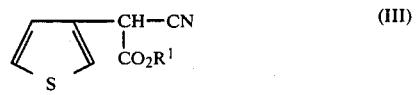
(III)

where $R^1$ represents an alkyl or aryl group, with at least a molar excess of an alkali metal hydroxide.

In compound (III), the group $R^1$ may suitably be $C_{1-6}$ alkyl, phenyl or substituted phenyl. The group $R^1$ is preferably $C_{1-6}$ alkyl, for example methyl or ethyl, especially ethyl.

The compound (III) may be prepared by conventional methods, for example by treatment of 3-thienylacetonitrile with a compound of formula $R^1O.CO.OR^1$ in the presence of a strong base such as sodium methoxide.

The process of the present invention employs an alkali metal hydroxide. Suitable such hydroxides include sodium hydroxide and potassium hydroxide. The most suitable solvent for the reaction is water although it is possible to add a co-solvent. The reaction is preferably carried out at a temperature greater than 40° C. In general if the temperature is maintained at 75° to 80° C. the hydrolysis is complete in about 2 to 2.5 hours. At a higher temperature, for example 100° to 110° C., the time of the hydrolysis is reduced to about 30 to 40 minutes.

It is preferred that a means is provided for removing ammonia vapour which is evolved during the reaction of the invention. This may be achieved for example by blowing an inert gas such as nitrogen through the reaction mixture or by evacuating the space above the reaction mixture. If no such means if provided for removing the ammonia, the process proceeds more slowly.

After the hydrolysis reaction is complete the 3-thienylmalonic acid may be isolated by conventional techniques for example by neutralisation with an acid, suitably hydrochloric acid, and solvent extraction.

The conversion of 3-thienylmalonic acid to a penicillin of formula (I) may be carried out by any convenient method. In particular those methods described in British Patent Specification Nos. 1,004,670, 1,125,557, 1,133,886 and 1,197,973 may be used to advantage.

The following Example illustrates the present invention.

EXAMPLE 1

Preparation of 3-Thienylmalonic Acid

To a reactor, which was vented directly to an acid scrubber, water (114 l) and sodium hydroxide flake (40 Kg) were charged. The mixture was stirred and the temperature rose rapidly from 20° to ca. 90° C. as the sodium hydroxide dissolved. The temperature was adjusted to 75° C. and ethyl-3-thienyl cyanoacetate (48.6 Kg of crude liquor containing approx. 50% cyanoacetate) was charged over a period of 15 minutes. The ensuing reaction was quite exothermic and the temperature was maintained at 80°–85° C. with water cooling.

After stirring for 15 minutes the vessel was carefully evacuated in order to remove the ammonia formed during the hydrolysis. Within a few minutes the temperature began to drop and was maintained at 77° C. with steam heating and full vacuum (ca. 100 mm) could be applied. Any solvent vapour which passed through the condenser was collected in a cardice trap, and the volume in the reactor was kept constant by the continuous addition of an equivalent volume of water. This procedure continued for 2.5 hours.

The reactor was again vented directly to the scrubber and the contents cooled at 30° C. Methyl isobutyl ketone (40 l) was charged and the excess sodium hydroxide was neutralised by addition of 10N hydrochloric acid (ca. 80 l), cooling being required to keep the temperature below 30° C.

Once the frothing subsided the pH was adjusted to 5.7 and the organic and aqueous phases separated. The organic phase was discarded. The aqueous phase was washed twice with methyl isobutyl ketone (1×40 l, 1×20 l) before being treated with charcoal [Norit S X plus (6 Kg)] for 15 minutes.

The charcoal was removed by centrifugation through a celite bed and the clear, pale yellow liquor transferred to a glassed steel reactor. The pH was adjusted to 3.5 with 10N hydrochloric acid (ca. 7 l), and the solution washed with methylene dichloride (1×40 l, 2×20 l).

The solution was now cooled to 5° C. and the pH adjusted to 1.0 with 10N hydrochloric acid (ca. 10 l). The liberated product was extracted into diethyl ether (1×40 l, 3×20 l) and these ether extracts were bulked and dried over magnesium sulphate and treated concurrently with Norit S X plus (1 Kg) for 2 hours. The aqueous liquors were discarded.

The magnesium sulphate and Norit S X plus were removed by filtration and the filtrate, together with washings (diethyl ether 2×10 l) were charged to a glassed steel digester where the ether was removed by distillation. The temperature was kept below 50° C. during this operation, a high vacuum pump being used towards the end of the distillation to remove the last traces of ether.

The residual 3-thienylmalonic acid remaining in the digester was broken down to a fine powder and slurried in methylene dichloride (40 l) for at least 4 hours. The product was then filtered via a centrifuge and washed with methylene dichloride (3×10 l), before being trayed and dried in the oven for 4 hours at 50° C.

An average yield of 18.8 Kg (101M) was obtained which represented a yield of approximately 78.5% of theory. The product was normally a white/cream solid with the following characteristics:
Melting point: 136°-138° C.
Water content: 0.1%
Equivalent weight: 93.0
Sodium chloride content: 0.1%.

We claim:
1. A hydrolytic process for the preparation in one step of 3-thienylmalonic acid from 3-thienyl cyanoacetate in enhanced yield and purity, said 3-thienylmalonic acid having the formula:

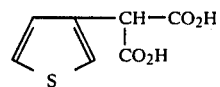

which comprises hydrolysing a compound of the formula:

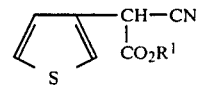

wherein $R^1$ is alkyl or aryl, with at least a molar excess over the amount theoretically required for hydrolysis of sodium or potassium hydroxide in an aqueous solvent.

2. A hydrolytic process according to claim 1, wherein the amount of sodium hydroxide with relation to the amount of 3-thienyl cyanoacetate is in the relative proportions of 40 kg:24 kg. and the hydrolysis is carried out at a temperature greater than 40° C.

3. A process according to claim 1, wherein $R^1$ is alkyl of 1 to 6 carbon atoms or phenyl.

4. A process according to claim 1, wherein $R^1$ is methyl or ethyl.

5. A process according to claim 1, wherein the hydroxide is sodium hydroxide and the compound hydrolysed is ethyl-3-thienyl cyanoacetate.

* * * * *